(12) United States Patent
Bruinsma et al.

(10) Patent No.: US 7,173,270 B1
(45) Date of Patent: Feb. 6, 2007

(54) DETECTOR SYSTEM FOR DETECTING A HEIGHT OF A PARTICLE, AND LITHOGRAPHIC APPARATUS AND DEVICE MANUFACTURING METHOD INCLUDING THE SAME.

(75) Inventors: Anastasius Jacobus Anicetus Bruinsma, Delft (NL); Pieter Johannes Marius Van Groos, Geldrop (NL); Jan Frederick Hoogkamp, Breda (NL); Kees Moddemeijer, Leiden (NL); Folkert Draaisma, Delft (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 11/229,832

(22) Filed: Sep. 20, 2005

(51) Int. Cl.
  *G01N 21/88* (2006.01)
  *G01B 11/06* (2006.01)
(52) U.S. Cl. ............... 250/559.41; 250/559.4; 250/559.45; 250/559.46; 250/559.27; 250/234; 356/237.3; 356/237.4; 356/239.8
(58) Field of Classification Search ............ 250/559.4, 250/559.41, 559.45, 559.46, 559.27, 559.38, 250/548, 234; 382/144, 145, 147, 149; 356/237.1–237.5, 356/239.8, 335–338, 630; 345/192; 355/53, 355/55, 68; 348/125, 126, 128
See application file for complete search history.

(56) References Cited

U.S. PATENT DOCUMENTS

| 6,031,607 A | * | 2/2000 | Miyazaki | 356/237.1 |
| 6,226,079 B1 | * | 5/2001 | Takeda et al. | 356/237.2 |
| 6,384,909 B2 | * | 5/2002 | Tomita et al. | 356/237.1 |
| 6,521,889 B1 | * | 2/2003 | Ina et al. | 250/306 |
| 6,597,448 B1 | * | 7/2003 | Nishiyama et al. | 356/237.4 |
| 6,683,683 B2 | * | 1/2004 | Tomita et al. | 356/237.2 |
| 6,797,975 B2 | * | 9/2004 | Nishiyama et al. | 250/559.04 |
| 2002/0047097 A1 | * | 4/2002 | Nishiyama et al. | 250/559.4 |
| 2002/0122174 A1 | * | 9/2002 | Hamamatsu et al. | 356/237.2 |
| 2004/0012775 A1 | * | 1/2004 | Kinney et al. | 356/237.2 |
| 2004/0041104 A1 | * | 3/2004 | Liebregts et al. | 250/492.22 |

* cited by examiner

*Primary Examiner*—Thanh X. Luu
*Assistant Examiner*—Davienne Monbleau
(74) *Attorney, Agent, or Firm*—Pillsbury Winthrop Shaw Pittman, LLP

(57) ABSTRACT

A lithographic apparatus transfers a pattern from a patterning device onto a substrate and includes a projection system to project a patterned radiation beam onto the substrate; a controllable actuator to adjust a distance between the projection system and the substrate; and a particle detector system to detect a particle on a surface of the substrate. The particle detector system has illumination optics directing the radiation to a detection area of the surface of the substrate, detection optics receiving radiation from the detection area of the surface of the substrate, and a detector coupled to the detection optics to produce a measurement signal. The apparatus further has a processing system to determine the height of a particle from the measurement signal, generate a height excess signal if the height exceeds a threshold value, and control the actuator in response to the height excess signal.

26 Claims, 7 Drawing Sheets

DETECTOR SYSTEM FOR DETECTING A HEIGHT OF A PARTICLE, AND LITHOGRAPHIC APPARATUS AND DEVICE MANUFACTURING METHOD INCLUDING THE SAME.

BACKGROUND

1. Field of the Invention

The present invention relates to a particle detector system. Also, the present invention relates to a lithographic apparatus comprising such particle detector system. The particle detector system may be used for detection of unwanted particles on a substrate before or during patterning of the substrate in a lithographic apparatus. Further, the present invention relates to a particle detecting method, and a device manufacturing method.

2. Description of the Related Art

A lithographic apparatus is a machine that applies a desired pattern onto a substrate or part of a substrate. A lithographic apparatus may be used, for example, in the manufacture of flat panel displays (FPDs), integrated circuits (ICs) and other devices involving fine structures. In a conventional apparatus, a patterning device, which may be referred to as a mask or a reticle, may be used to generate a circuit pattern corresponding to an individual layer of a flat panel display (or other device). This pattern may be transferred on (part of) the substrate (e.g., a glass plate), for instance via imaging onto a layer of radiation-sensitive material (resist) provided on the substrate.

Instead of a circuit pattern, the patterning device may be used to generate other patterns, for example a color filter pattern, or a matrix of dots. Instead of a mask, the patterning device may comprise a patterning array that comprises an array of individually controllable elements. A benefit of such a system compared to a mask-based system is that the pattern can be changed more quickly and for less cost.

A flat panel display substrate may be rectangular in shape. Lithographic apparatus designed to expose a substrate of this type may provide an exposure region which covers a full width of the rectangular substrate, or which covers a portion of the width (for example half of the width). The substrate may be scanned underneath the exposure region, while the mask or reticle is synchronously scanned by the projection beam. In this way, the pattern is transferred to the substrate. If the exposure region covers the full width of the substrate then exposure may be completed with a single scan. If the exposure region covers, for example, half of the width of the substrate, then the substrate may be moved transversely after the first scan, and a further scan is typically performed to expose the remainder of the substrate.

Current systems for Flat Panel Displays (FPD) lithography use a mask that is imaged onto a substrate, as described above. In maskless FPD lithography systems, a part of the lithographic apparatus—usually an imaging system or an optical component thereof, such as a lens—is arranged relatively close to the substrate which is moving during imaging. The distance between the imaging system and the substrate may be in the order of several mm or less, down to for instance 0.1 mm. If particles or other contamination (which will be deemed to be included in the term "particle" used herein) are present at the substrate surface, they may damage the imaging system during passage thereof when they have a height (a dimension perpendicular to the substrate surface) which exceeds the distance between the imaging system and the substrate. Such damage will incur relatively high costs, for instance for replacing at least part of the imaging system but above all due to a decrease in production caused by the downtime of the lithographic apparatus. The particles may include, but are not limited to, glass particles, resulting from machining and handling a glass substrate. The relatively high travel speed of the substrates used for FPD production, in the order of meters per second (m/s), as well as the relatively large dimensions of the substrates, in the order of meters, both in width and in length, may further complicate the manufacturing process.

SUMMARY

It is desirable to provide a particle detector system and a method for detection of a particle on the surface of a substrate.

According to an embodiment of the invention, there is provided a lithographic apparatus arranged to transfer a pattern from a patterning device onto a substrate, the apparatus comprising a particle detector system for detecting a particle on a surface of the substrate, the particle detector system comprising: a radiation source configured to generate radiation; illumination optics configured to direct the radiation generated by the radiation source to a detection area of the surface of the substrate; detection optics configured to receive radiation from the detection area of the surface of the substrate; and a detector coupled to the detection optics for producing at least one measurement signal, the apparatus further comprising a processing system configured to determine the height of a particle from the at least one measurement signal, and to generate a height excess signal if the height exceeds a threshold value.

According to an embodiment of the invention, there is provided a particle detector system for detecting a particle on a surface of a substrate, the particle detector system comprising: a radiation source configured to generate radiation; illumination optics configured to direct the radiation generated by the radiation source to a detection area of the surface of the substrate; detection optics configured to receive radiation from the detection area of the surface of the substrate; and a detector coupled to the detection optics for producing at least one measurement signal, a processing system coupled to the detector, the processing system configured to determine the height of a particle from the at least one measurement signal, and to generate a height excess signal if the height exceeds a threshold value.

According to an embodiment of the invention, there is provided a method for detecting a particle on a surface of a substrate, the method comprising: generating radiation; directing the radiation to a detection area of the surface of the substrate; detecting radiation from the detection area of the surface of the substrate; producing at least one measurement signal from the detected radiation, determining the height of a particle from the at least one measurement signal; and generating a height excess signal if the height exceeds a threshold value.

According to an embodiment of the invention, there is provided a device manufacturing method comprising: providing a substrate; projecting a patterned beam of radiation on a surface of the substrate; the method further comprising: detecting a particle on the surface of the substrate according to the above method; and, if a particle is detected, using the height excess signal to reject at least a part of the substrate.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
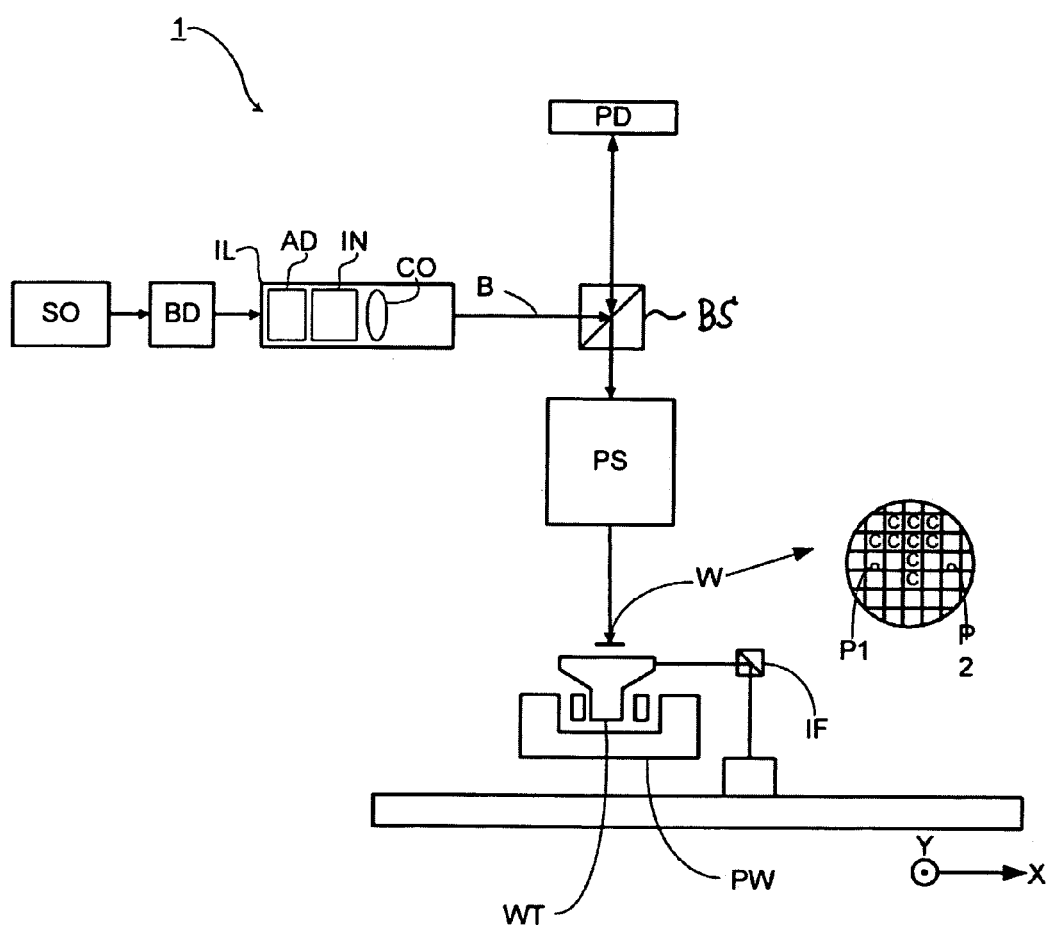
FIG. 1 depicts a lithographic apparatus.

FIG. 1 schematically depicts an example of a lithographic apparatus 1. The apparatus comprises:

an illumination system (illuminator) IL configured to condition a radiation beam B (e.g., UV radiation);

a substrate table WT constructed to support a substrate (e.g., a resist-coated substrate) W and connected to a positioner PW configured to accurately position the substrate W in accordance with certain parameters; and a projection system (e.g., a refractive projection lens system) PS configured to project the beam of radiation B modulated by a patterning device PD onto a target portion C (e.g., comprising one or more dies) of the substrate W.

In general the patterning device PD will be fixed relative to the projection system PS; however it may instead be connected to a positioner configured to accurately position the patterning device PD accordance with certain parameters. The illumination system IL may include various types of optical components, such as refractive, reflective, magnetic, electromagnetic, electrostatic or other types of optical components, or any combination thereof, for directing, shaping, or controlling radiation.

The term "patterning device", used herein should be broadly interpreted as referring to any device that can be used to modulate the cross-section of a radiation beam such as to create a pattern in a target portion of the substrate. It should be noted that the pattern imparted to the radiation beam may not exactly correspond to the desired pattern in the target portion of the substrate, for example if the pattern includes phase-shifting features or so called assist features. Similarly, the pattern eventually generated on the substrate may not correspond to the pattern formed at any one instant on the array of individually controllable elements. This may be the case in an arrangement in which the eventual pattern formed on each part of the substrate is built up over a given period of time or a given number of exposures during which the pattern on the array of individually controllable elements and/or the relative position of the substrate changes. Generally, the pattern created on the target portion of the substrate will correspond to a particular functional layer in a device being created in the target portion, such as an integrated circuit or a flat panel display (e.g., a color filter layer in a flat panel display or a thin film transistor layer in a flat panel display). Examples of such patterning devices include, e.g., reticles, programmable mirror arrays, laser diode arrays, light emitting diode arrays, grating light valves, and LCD arrays. Patterning devices whose pattern is programmable with the aid of an electronic device (e.g., a computer), such as patterning devices comprising a plurality of programmable elements (e.g., all the devices mentioned in the previous sentence except for the reticle), are collectively referred to herein as "contrast devices."

The lithographic apparatus may comprise one or more contrast devices. For example, it may have a plurality of arrays of individually controllable elements, each controlled independently of each other. In such an arrangement, some or all of the arrays of individually controllable elements may have at least one of a common illumination system (or part of an illumination system), a common support structure for the arrays of individually controllable elements and/or a common projection system (or part of the projection system).

In an embodiment, such as the embodiment depicted in FIG. 1, the substrate W has a substantially circular shape, optionally with a notch and/or a flattened edge along part of its perimeter. In an embodiment, the substrate has a polygonal shape, e.g., a rectangular shape.

In an embodiment, the substrate W is a wafer, for instance a semiconductor wafer. In an embodiment, the wafer material is selected from the group consisting of Si, SiGe, SiGeC, SiC, Ge, GaAs, InP, and InAs. In one embodiment, the wafer is a III/V compound semiconductor wafer. In an embodiment, the wafer is a silicon wafer. In an embodiment, the substrate is a ceramic substrate. In an embodiment, the substrate is a glass substrate. In an embodiment, the substrate is a plastic substrate. In an embodiment, the substrate is transparent (for the naked human eye). In an embodiment, the substrate is colored. In an embodiment, the substrate is absent a color. The thickness of the substrate may vary and, to an extent, may depend, e.g., on the substrate material and/or the substrate dimensions. In an embodiment, the thickness is at least 50 µm, for instance at least 100 µm, at least 200 µm, at least 300 µm, at least 400 µm, at least 500 µm, or at least 600 µm. In one embodiment, the thickness of the substrate is at most 5000 µm, for instance at most 3500 µm, at most 2500 µm, at most 1750 µm, at most 1250 µm, at most 1000 µm, at most 800 µm, at most 600 µm, at most 500 µm, at most 400 µm, or at most 300 µm. The substrate referred to herein may be processed, before or after exposure, in for example a track (a tool that typically applies a layer of resist to a substrate and develops the exposed resist), a metrology tool and/or an inspection tool. In an embodiment, a resist layer is provided on the substrate. The surface of the substrate may reflect at least part of any radiation directed to it.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system."

The projection system may image the pattern on an array of individually controllable elements such that the pattern is coherently formed on the substrate; alternatively, the projection system may image secondary sources for which the elements of the array of individually controllable elements act as shutters. In this respect, the projection system may comprise an array of focusing elements such as a micro lens array (known as an MLA) or a Fresnel lens array, e.g., to form the secondary sources and to image spots onto the substrate. In an embodiment, the number of individually controllable elements in the patterning device is equal to or greater than the number of focusing elements in the array of focusing elements. In an embodiment, one or more of the focusing elements in the array of focusing elements may be optically associated with one or more of the individually controllable elements in the array of individually controllable elements. In an embodiment, the MLA is movable (e.g., with the use of actuators) at least in the direction to and away from the substrate, e.g., with the use of one or more actuators. Being able to move the MLA to and away from the substrate allows, e.g., for focus adjustment without having to move the substrate.

As here depicted, the apparatus is of a reflective type (e.g., employing a reflective array of individually controllable elements). Alternatively, the apparatus may be of a transmissive type (e.g., employing a transmissive array of individually controllable elements).

The lithographic apparatus may be of a type having two (dual stage) or more substrate tables. In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by an "immersion liquid" having a relatively high refractive index, e.g., water, so as to fill a space between the projection system and the substrate. An immersion liquid may also be applied to other spaces in the lithographic apparatus, for example, between the patterning device and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam to have a desired uniformity and intensity distribution in its cross-section. The illuminator IL, or an additional component associated with it, may also be arranged to divide the radiation beam into a plurality of sub-beams that may, for example, each be associated with one or a plurality of the individually controllable elements of the array of individually controllable elements. A two-dimensional diffraction grating may, for example, be used to divide the radiation beam into sub-beams. In the present description, the terms "beam of radiation" and "radiation beam" encompass, but are not limited to, the situation in which the beam is comprised of a plurality of such sub-beams of radiation.

The radiation beam B is incident on the patterning device PD (e.g., an array of individually controllable elements) and is modulated by the patterning device. Having been reflected by the patterning device PD, the radiation beam B passes through the projection system PS, which focuses the beam onto a target portion C of the substrate W. With the aid of the positioner PW and position sensor IF (e.g., an interferometric device, linear encoder or capacitive sensor), the substrate table WT can be moved accurately, e.g., so as to position different target portions C in the path of the radiation beam B. Where used, the positioner for the array of individually controllable elements can be used to correct accurately the position of the patterning device PD with respect to the path of the beam B, e.g., during a scan. In an embodiment, movement of the substrate table WT is realized with the aid of a long-stroke module (course positioning) and a short-stroke module (fine positioning), which are not explicitly depicted in FIG. 1. In an embodiment, the apparatus is absent at least a short stroke module for moving substrate table WT. A similar system may also be used to position the array of individually controllable elements. It will be appreciated that the projection beam B may alternatively/additionally be moveable while the object table and/or the array of individually controllable elements may have a fixed position to provide the required relative movement. Such an arrangement may assist in limiting the size of the apparatus. As a further alternative, which may, e.g., be applicable in the manufacture of flat panel displays, the position of the substrate table WT and the projection system PS may be fixed and the substrate W may be arranged to be moved relative to the substrate table WT. For example, the substrate table WT may be provided with a system for scanning the substrate W across it at a substantially constant velocity.

As shown in FIG. 1, the beam of radiation B may be directed to the patterning device PD using a beam splitter BS configured such that the radiation is initially reflected by the beam splitter BS and directed to the patterning device PD. It should be realized that the beam of radiation B may also be directed at the patterning device without the use of a beam splitter. In an embodiment, the beam of radiation is directed at the patterning device PD at an angle between about 0 and 90° (the embodiment shown in FIG. 1 is at a 90° angle). The patterning device PD modulates the beam of radiation B and reflects it back to the beam splitter BS which transmits the modulated beam to the projection system PS. It will be appreciated, however, that alternative arrangements may be used to direct the beam of radiation B to the patterning device PD and subsequently to the projection system PS. In particular, an arrangement such as is shown in FIG. 1 may not be required if a transmissive patterning device is used.

The depicted apparatus can be used in four preferred modes:

1. In step mode, the array of individually controllable elements and the substrate are kept essentially stationary, while an entire pattern imparted to the radiation beam is projected onto a target portion C at one go (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the array of individually controllable elements and the substrate are scanned synchronously while a pattern imparted to the radiation beam is projected onto a target portion C (i.e., a single dynamic exposure). The velocity and direction of the substrate relative to the array of individually controllable elements may be determined by the (de-) magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In pulse mode, the array of individually controllable elements is kept essentially stationary and the entire pattern is projected onto a target portion C of the substrate W using a pulsed radiation source. The substrate table WT is moved with an essentially constant speed such that the projection beam B is caused to scan a line across the substrate W. The pattern on the array of individually controllable elements is updated as required between pulses of the radiation system and the pulses are timed such that successive target portions C are exposed at the required locations on the substrate W. Consequently, the projection beam B can scan across the substrate W to expose the complete pattern for a strip of the substrate. The process is repeated until the complete substrate W has been exposed line by line.

4. In continuous scan mode, essentially the same as pulse mode except that the substrate W is scanned relative to the modulated beam of radiation B at a substantially constant speed and the pattern on the array of individually controllable elements is updated as the projection beam B scans across the substrate W and exposes it. A substantially constant radiation source or a pulsed radiation source, synchronized to the updating of the pattern on the array of individually controllable elements may be used.

Combinations and/or variations on the above described modes of use or entirely different modes of use may also be employed.

Figure 2:
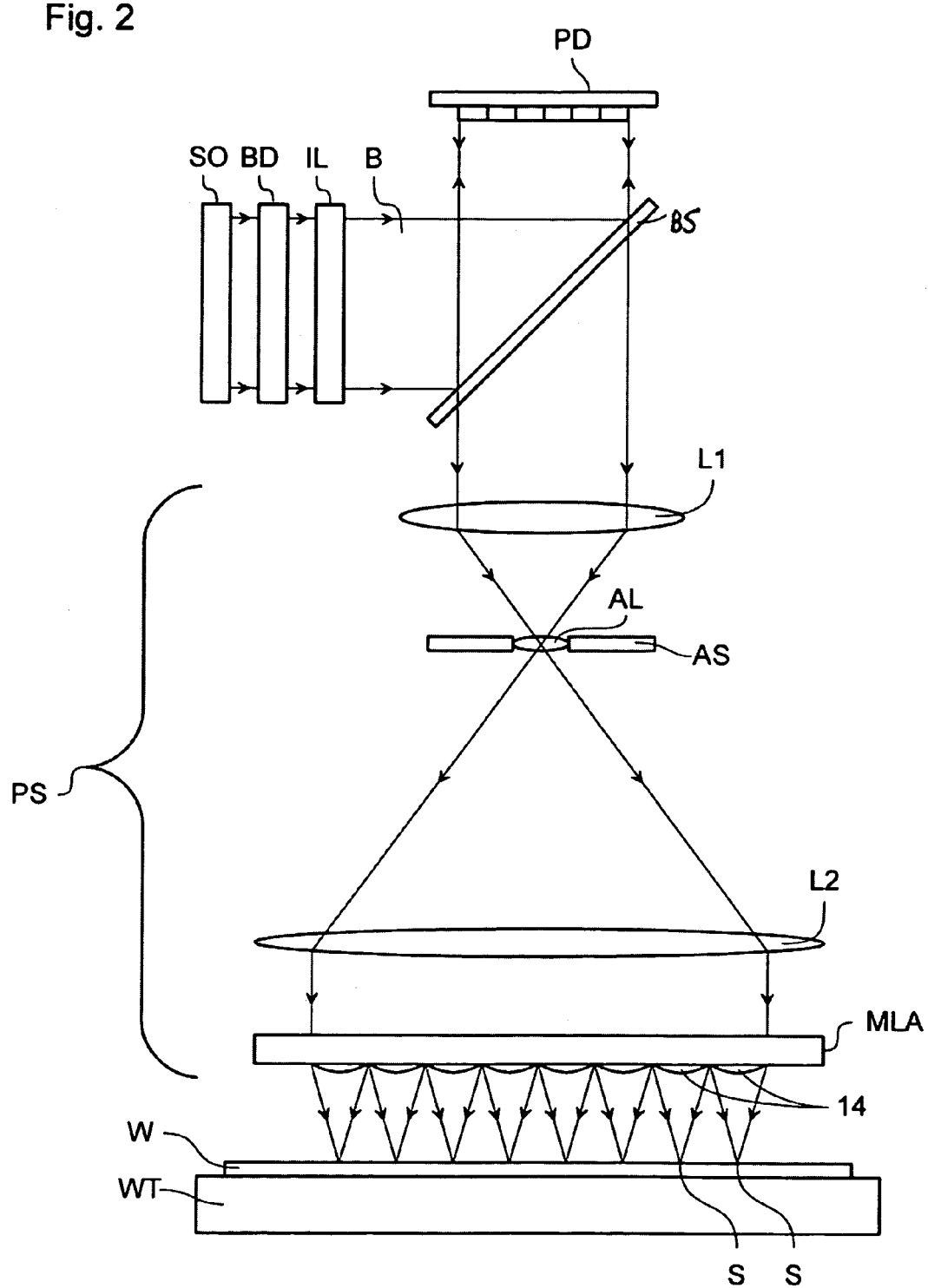
FIG. 2 depicts a lithographic apparatus according to an embodiment of the invention.

FIG. 2 depicts an arrangement of the apparatus according to an embodiment of the present invention that may be used, e.g., in the manufacture of flat panel displays. Components corresponding to those shown in FIG. 1 are depicted with the same reference numerals. Also, the above descriptions of the various embodiments, e.g., the various configurations of the substrate, the contrast device, the MLA, the beam of radiation, etc., remain applicable.

As shown in FIG. 2, the projection system PS includes a beam expander, which comprises two lenses L1, L2. The first lens L1 is arranged to receive the modulated radiation beam B and focus it through an aperture in an aperture stop AS. A further lens AL may be located in the aperture. The radiation beam B then diverges and is focused by the second lens L2 (e.g., a field lens).

The projection system PS further comprises an array of lenses MLA arranged to receive the expanded modulated radiation B. Different portions of the modulated radiation beam B, corresponding to one or more of the individually controllable elements in the patterning device PD, pass through respective different lenses in the array of lenses MLA. Each lens focuses the respective portion of the modulated radiation beam B to a point which lies on the substrate W. In this way an array of radiation spots S is exposed onto the substrate W. It will be appreciated that, although only eight lenses of the illustrated array of lenses 14 are shown, the array of lenses may comprise many thousands of lenses (the same is true of the array of individually controllable elements used as the patterning device PD).

Figure 3:
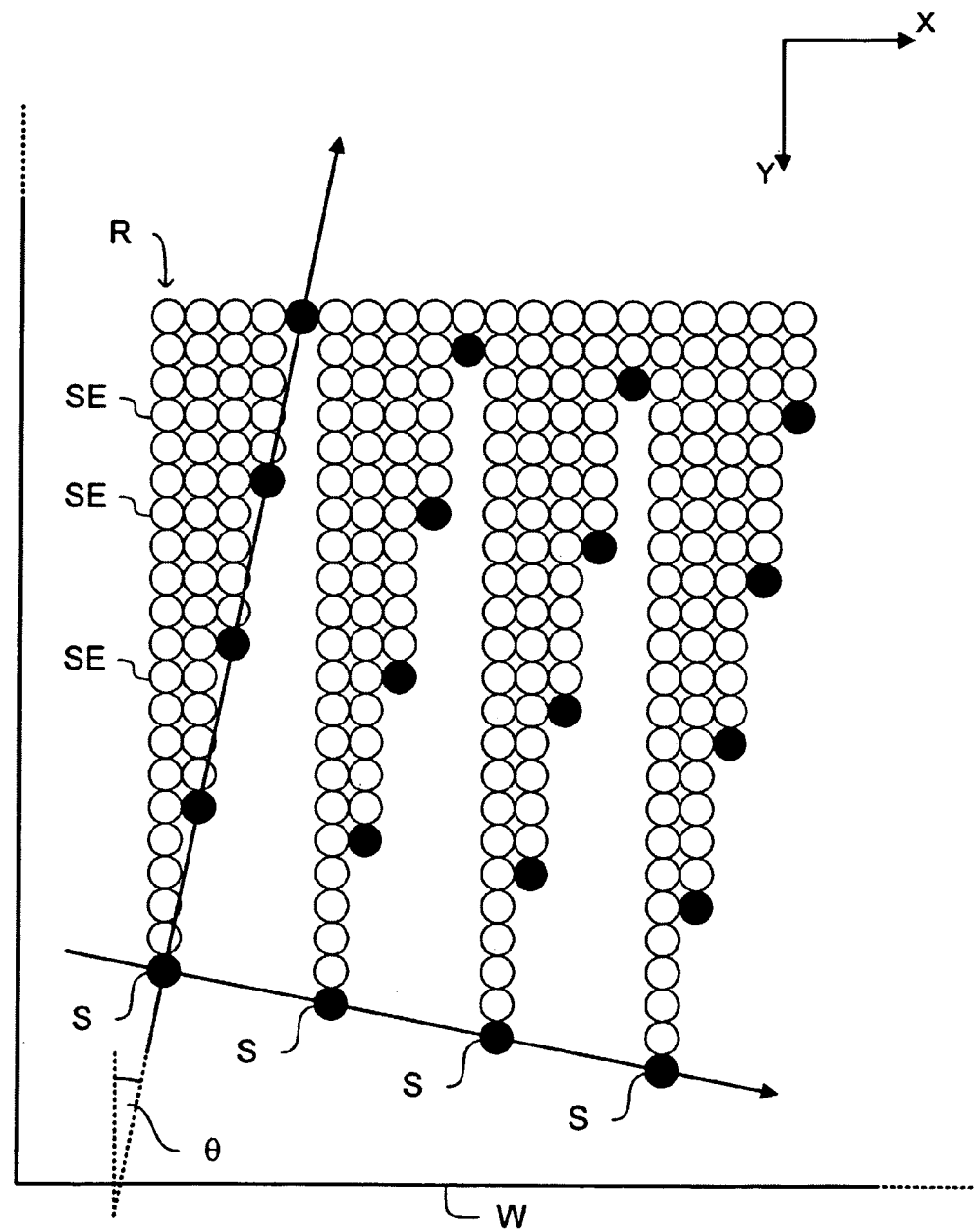
FIG. 3 depicts a mode of transferring a pattern to a substrate using a lithographic apparatus as shown in FIG. 2.

FIG. 3 illustrates schematically how the pattern on the substrate W may be generated. The filled in circles represent the array of spots S projected onto the substrate by the array of lenses MLA in the projection system PS. The substrate is moved relative to the projection system in the Y direction as a series of exposures are exposed on the substrate. The open circles represent spot exposures SE that have previously been exposed on the substrate. As shown, each spot projected onto the substrate by the array of lenses within the projection system PS exposes a row R of spot exposures on the substrate W. The complete pattern for the substrate is generated by the sum of all the rows R of spot exposures SE exposed by each of the spots S. Such an arrangement is commonly referred to as "pixel grid imaging."

It can be seen that the array of radiation spots S is arranged at an angle $\theta$ relative to the substrate W (the edges of the substrate lie parallel to the X and Y directions). This is done so that when the substrate is moved in the scanning direction (the Y-direction), each radiation spot will pass over a different area of the substrate, thereby allowing the entire substrate to be covered by the array of radiation spots S.

Figure 4:
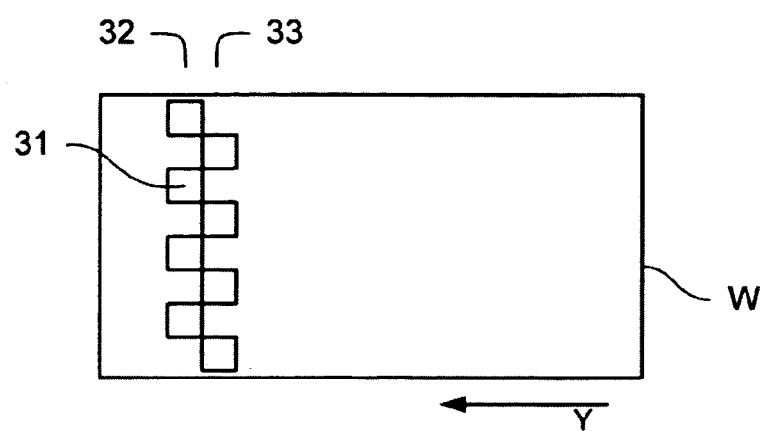
FIG. 4 depicts an arrangement of optical engines in accordance with an embodiment of the invention.

FIG. 4 shows schematically how the entire flat panel display substrate W may be exposed in a single scan, by using a plurality of optical engines. Eight arrays 31 of radiation spots S are produced by eight optical engines (not shown), arranged in two rows 32, 33 in a 'chess board' configuration such that the edge of one array of radiation spots S slightly overlaps (in the scanning direction Y) with the edge of the adjacent array of radiation spots 15. In an embodiment, the optical engines are arranged in at least 3 rows, for instance 4 rows or 5 rows. In this way, a band of radiation extends across the width of the substrate W, allowing exposure of the entire substrate to be performed in a single scan. It will be appreciated that any suitable number of optical engines may be used.

Each optical engine may comprise a separate illumination system IL, patterning device PD and projection system PS as described above. It is to be appreciated, however, that two or more optical engines may share at least a part of one or more of the illumination system, patterning device and projection system.

Figure 5:
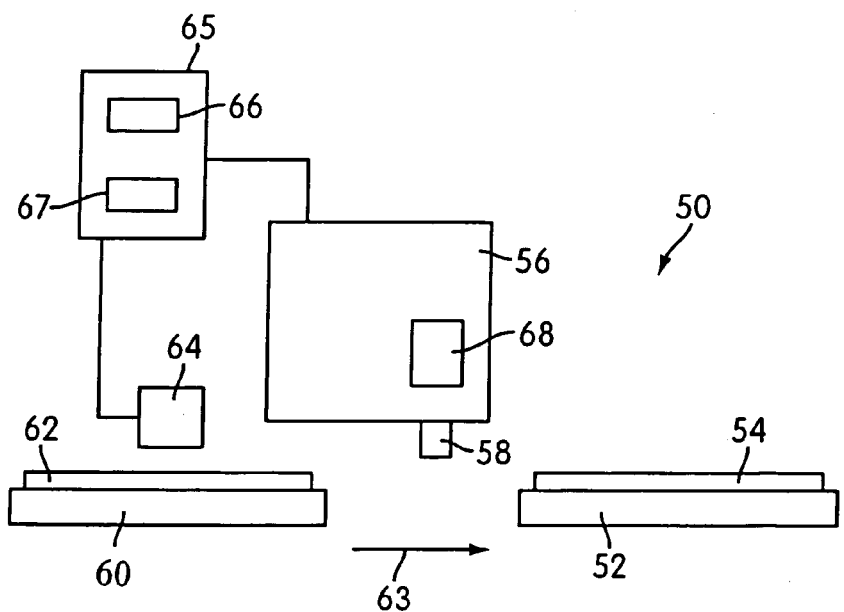
FIG. 5 depicts a schematic view of a lithographic apparatus according to an embodiment of the invention.

Referring to FIG. 5, a lithographic apparatus 50 for the production of for instance Flat Panel Displays (as discussed above in more detail with reference to FIG. 14) comprises two substrate tables or stages. The lithographic apparatus further comprises a projection system 56, including a lens or a lens array 58, for patterning the substrates. A first stage 52 carries a first substrate 54, and a second stage 60 carries a second substrate 62. The first stage 52 may be moved relative to the projection system 56 for patterning the substrate 54. The first stage 52 and/or the second stage 60 are driven, for instance, in the direction of arrow 63 or in the reverse direction. The first stage 52 and second stage 60 may be provided with a suction device for holding the substrates onto the stages by means of a vacuum.

The substrates 54, 62 may be moved in the lithographic apparatus 50 at a rate in the order of several meters per second (m/s), for instance in the order of 2–3 m/s. The dimensions of the substrates 54, 62 may be several meters, both in width as in length. Several Flat Panel Displays may be fabricated from one substrate. The substrate may therefore have a width of for instance 2 to 3 m, and a length of for instance 4 to 8 m.

A distance in vertical direction (i.e., in a direction perpendicular to the (upper) surface of the substrate) between the lens or lens array 58 and the substrate 54 may be in the order of several mm or less, down to for instance 0.1 mm. Particles, or other contamination, that may be present at the substrate surface and that have a height (i.e., a dimension measured perpendicular to the surface of the substrate) which exceeds the above-mentioned distance can damage the imaging system, i.e. lens or lens array 58. Particles having a height that is smaller than the distance between the lens array and the substrate may pass the lens array without damaging it. The particles may include, but are not limited to, glass particles, resulting from machining or handling a glass substrate.

The lens or lens array 58 is relatively expensive, and damage thereof would incur high costs. The surface of the lenses of the lens array may be coated, and particles may scratch such coating, which would deteriorate the patterning quality or even completely nullify the yield. Also, the downtime of the lithographic apparatus, for replacing the lens array, would reduce the production of FPDs. The above effects in any combination will incur considerable expenses.

To prevent damage of the lens or lens array 58, particles need to be detected at the substrate surface. The main interest is a measurement of the height of particles.

Referring again to FIG. 5, the lithographic apparatus 50 includes a particle detector 64 for detection of particles and other contamination at the surface of the substrate 62. The stage 60 is moved in the direction of arrow 63 or the opposite direction for a detection of particles at the surface of the substrate 62 before the substrate 62 is transferred to the stage 52 for patterning. The particle detector 64 is coupled to a processing system or computer 65, which includes a central processing unit 66 and a memory 67. The computer 65 is arranged for calculating the height of particles and is actively coupled to the projection system 56. The computer 65 may be dedicated to particle detection, or may be (or form part of) a processing system also performing other tasks in the lithographic apparatus 50. The projection system 56 includes an actuator 68 for adjusting the distance between the lens or lens array 58 and a substrate 54, 62. Adjusting the distance includes lifting or lowering the lens or lens array 58.

During use, the particle detector 64 sends a measurement signal to computer 65, the measurement signal possibly containing data pertaining to particles present on substrate 62. If computer 65 computes from the measurement signal the presence of a particle on substrate 62 having a height or dimension that exceeds a certain predetermined threshold value, the computer produces a height excess signal or dimension excess signal which may be stored in the memory 67. The height excess signal or dimension excess signal may be used to reject the substrate 62, or to adjust the distance between lens or lens array 58 and the substrate 62 before or during patterning. A substrate 62 which is rejected may possibly be cleaned for further use. Also it may be envisaged that part of the substrate 62 is still usable, by determining the location of the contamination c.q. particle and using other parts of the substrate for patterning. Alternatively, if the computer 65 produces a height excess signal or dimension excess signal, the location of the particle causing the height excess signal is stored in the memory 67 of the computer 65. During patterning, the lens or lens array 58 may be lifted and subsequently lowered when the location of the particle passes the lens or lens array 58, to avoid contact between the particle and the lens or lens array 58. Alternatively, the lens or lens array 58 may be positioned in a non-operative position at a distance from the substrate during a detection of particles on the substrate, whereas the lens or lens array 58 is lowered to an operative position at a smaller distance relative to the substrate when no particles having a height exceeding a threshold have been detected.

As described above, a detection of particles is performed before patterning. However, such detection may also be performed during patterning, when the particle detector system may detect particles on a substrate being patterned.

Figure 6:
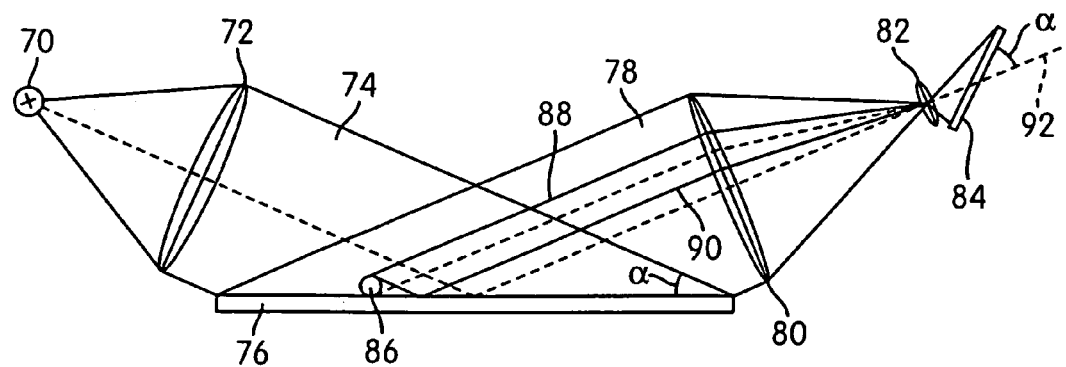
FIG. 6 depicts a schematic view of the optical components of a particle detector system according to a first embodiment of the invention.

Referring to FIG. 6, a particle detector comprises an illumination system or light source 70 that generates a beam 74 of light or other suitable radiation via a lens or a lens system 72 onto substrate 76. The light 74 arrives at the substrate 76 at an angle α in a detection area. In the absence of a particle, the light reflects in the detection area at the surface of the substrate 76. A beam 78 of reflected light is focussed by a second lens or lens system 80. A third lens or lens system 82 projects the beam 78 onto a detector or sensor array 84. The illumination system 70 is arranged on one side of the substrate 76 and the sensor array 84 is arranged on an opposite side of the substrate 76. The illumination optics consisting of lens system 72 are configured to direct the beam 74 of light at least from one side of the substrate to the opposite side thereof. Detection optics consisting or lens systems 80 and 82 are configured to receive the beam 78 of light at least from one side of the substrate to the opposite side thereof.

In an embodiment, the light source has a low numerical aperture, i.e., the light source essentially can be considered to be a point source. In a further embodiment, the illumination optics generate essentially parallel rays of light. In a further embodiment, the lens system 82 has a small numerical aperture or diaphragm. In a further embodiment, the detection optics are telecentric. The low numerical aperture of the light source in combination with the low numerical aperture of the detection optics, particles will generally be imaged as dark areas on a light background. Transparent particles scattering the light will also been imaged as a dark area, since such scattered light will not reach the detector 84 as a result of the low numerical aperture of the detection optics.

The detector 84 is arranged under an angle α with respect to a dashed centre line 92 of the detection optics. Due to this so-called Scheimpflug principle, the surface of the substrate illuminated by the beam 74 is in focus from one side of the substrate to the opposite side thereof, since the focal plane coincides essentially with the top surface of substrate 76. Essentially the whole illuminated surface of substrate 76 is in focus at once, and all objects (e.g., particle 86) at the substrate will be in focus at an image that is recorded by the sensor array 84. Also, all objects at the substrate having the same dimensions but being situated at different distances from the sensor array 84, appear with the same dimensions on the sensor array 84.

In a practical embodiment, the lens systems 72, 80 and 82 may comprise a single lens, or a plurality of lenses. The lens 72 has a diameter that is large enough to illuminate the entire width of substrate 76 with rays of light. The lens 80 has a diameter that is large enough to collect all the reflected rays of light 78. In an embodiment, lenses 72 and/or 80 may have a diameter in the order of 150 mm. The lens 82 has a diameter that is smaller that the diameter of lens 80 to increase the depth of focus. In other words, the numerical aperture of the detection optics, as determined by the lens 82, is relatively small. Light that is diffusely reflected—for instance at the surface of a particle 86—will therefore miss the lens 82, thus improving the contrast of the image recorded by sensor array 84. The lens 82 may have a diameter in the order of 10–20 mm.

A particle 86 may obstruct the light coming from the light source 70 to prevent it from reaching the sensor array 84, or it may deflect or scatter the light. In both cases, the particle 86 is detected by the sensor array as a dark area against an bright background. In between rays of light 88 and 90, the sensor array 84 will record a lower or no light intensity. It has to be kept in mind here that the light not falling on the particle 86 is reflected by the substrate. The relation between the dark area caused by the particle 86 and particle height is explained below, referring to FIG. 7.

The distance (as seen perpendicular to the surface of a substrate) between the lens or lens array of the projection system of the lithographic apparatus and the substrate during patterning may be in the order of 1 mm, down to about 0.1 mm. A substrate or part thereof will be rejected upon measurement of a particle having a height that is larger than for instance 0.7 times the distance between the lens array and the substrate.

The beam 74 arrives at the substrate surface at an angle $\alpha$. The angle $\alpha$ is preferably chosen to be relatively small, in the order between 0–5 degrees. In an embodiment, the angle $\alpha$ is selected between about 1–2 degrees. It is observed here that the arrangement of FIG. 6 illustrates a relatively large angle $\alpha$ with a substrate and a particle being shown out of proportions, solely for providing a clear view of the envisaged optical effects.

A relatively small angle $\alpha$ provides several benefits. A measurement using the particle detector of FIG. 6 determines the dimensions of particles by measuring the dark area they produce in beam 78. The dimension of the dark area in the image that is recorded by sensor array 84, is almost completely determined by the height of the particle and hardly by any other dimension of the particle.

Figure 7:
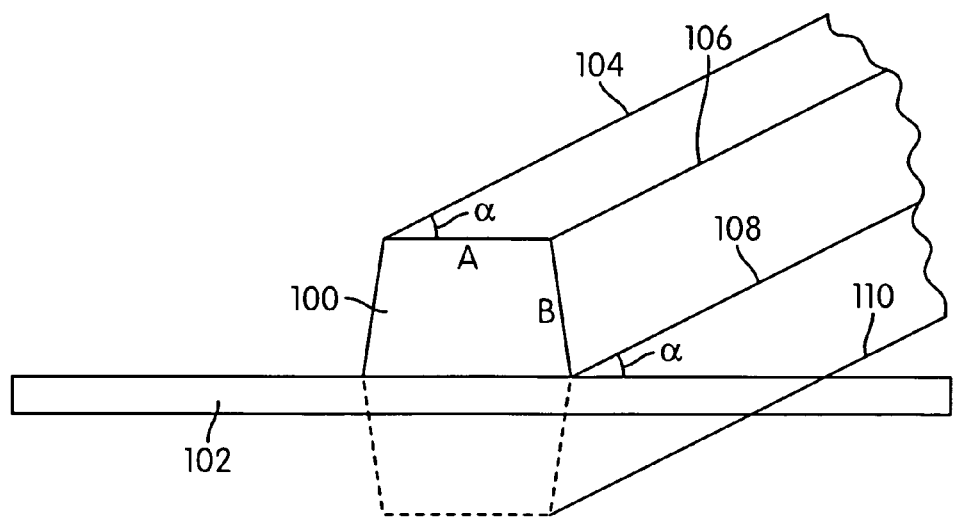
FIG. 7 depicts a schematic view of an exemplary particle on a substrate and rays of light.

Referring to FIG. 7, the above is explained in detail by examining an exemplary trapezium-like particle 100 that is arranged on a substrate 102. The lines 104, 106, 108 are straight parallel lines in the direction of the lens 80 of FIG. 6. Particle 100 has a width A and height B, where the width is defined as a dimension in the direction of the beams 74, 78 parallel to the (upper) surface of the substrate, and the height is defined as a dimension perpendicular to the (upper) surface of the substrate. The ratio between the height and the width of particle 100 that is measured using the above-described measurement method depends on angle $\alpha$. The ratio between the measured height and the measured width of the particle 100 is magnification (height)/magnification (width)=$\cos \alpha / \sin \alpha$. The smaller angle $\alpha$ is chosen, the larger the above ratio will be. For angle $\alpha=2$ degrees, $\cos \alpha / \sin \alpha = 28.6$. This indicates that the width of a particle contributes only to 1/28.6 times of its value to a length of a dark area observed by the detector 84. Depending on the desired accuracy, the value of angle $\alpha$ may be chosen such that in practice the height of a particle will trigger a rejection, i.e., if the height B exceeds a predetermined threshold value. Additionally, in practice the above ratio will be doubled due to the mirror image of the particle reflected in the substrate. The particle is mirrored by the substrate, as indicated with dashed lines in FIG. 7. As the light source 70 is arranged on one side of the substrate 76 and the detector 84 is arranged on the opposite side of the substrate, the dark area of the particle will be twice as long (FIG. 6). The particle detector will detect twice the actual height of the particle. This indicates that the height of a particle contributes twice to the length of the dark area observed by the detector.

Figure 9:
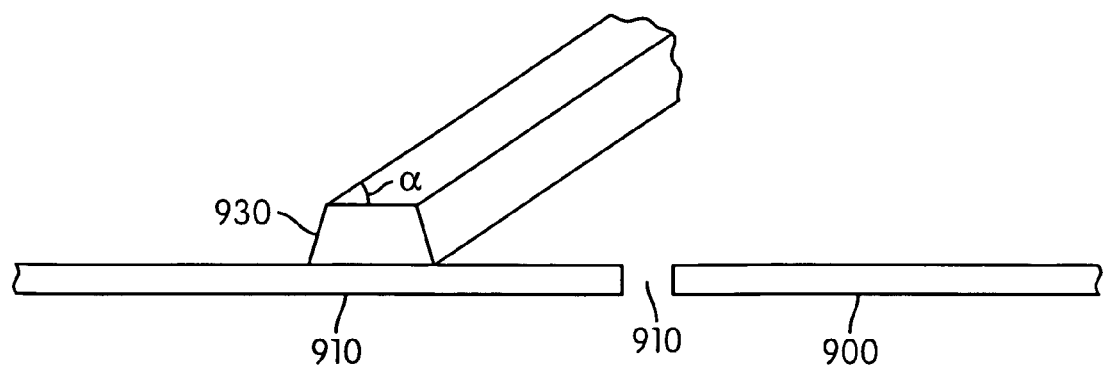
FIG. 9 depicts a schematic view of a substrate and a dummy substrate, which is positioned adjacent to the substrate.
Figure 10:
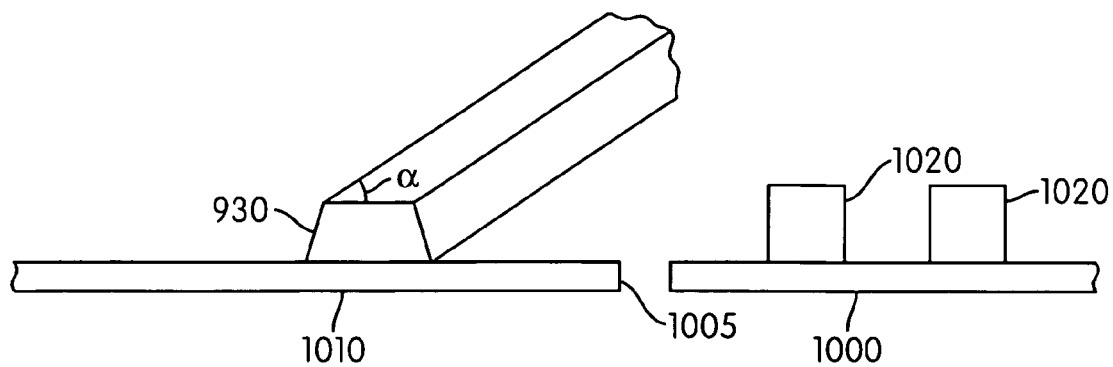
FIG. 10 depicts a schematic view of a substrate and a construction part, which is positioned adjacent to the substrate.

Close to a longitudinal edge of the substrate, the mirror image of a particle may, at least partially, be absent. In other words, close to the edges, part of the dark area falls outside the substrate, which results in a dark area not being representative of the actual height of the particle. To avoid such circumstances, and to enable the particle detector to provide meaningful measuring results also close to an edge of the substrate, different measures may be taken. In a first embodiment shown in FIG. 9, a dummy substrate part 900 having similar properties as the substrate 920 under consideration may be placed, e.g., stationary, next to the moving substrate 920 within the trajectory of the beam 78. Provided that a gap 910 between the substrate 920 and the dummy substrate part 900 is limited, a dark area generated by a particle 930, the dark area extending on the dummy substrate part, may be detected, provided that the particle detector covers both the substrate and the dummy substrate part. In a second embodiment, a particle detection may be performed both from one side of the substrate to the opposite side, as illustrated in FIG. 6, and in the reverse direction, e.g., by employing a second similar particle detector system having its components arranged accordingly. In a third embodiment, an edge of the substrate may be detected prior to a particle detection so that it is known whether a particle may be located in a critical edge area of the substrate or not. In a fourth embodiment, the threshold value in the area close to the substrate edge may be decreased to compensate for the edge effect. A detection of a particle having a height that is 0.35 times the distance between the substrate and a lens array within 1 to 3% of the substrate width may already initiate a rejection of the substrate. Another way of compensating for the above effect includes a gradual decrease of the threshold value in the direction of the edge of a substrate. In a fifth embodiment shown in FIG. 10, a construction part 1000 may be placed, e.g., stationary, next to the moving substrate 1010 within the trajectory of the beam 78. The construction part 1000 may be provided with a plurality of spaced non-reflecting lines 1020 essentially parallel to the edge 1005. The width of the lines may be selected to be smaller than a critical dark area corresponding with a threshold value in a measurement signal generated by the sensor array 84.

In a practical embodiment, the light source 70 may be a laser. The detector (sensor array) may comprise a camera. A camera frame rate may be in the range of 2 to 8 kHz. Alternatively, the detector may comprise a linear CCD array. The frame rate of such CCD array may be in the range of 10 to 20 kHz. Two or more of the above-described systems may be combined.

Figure 8:
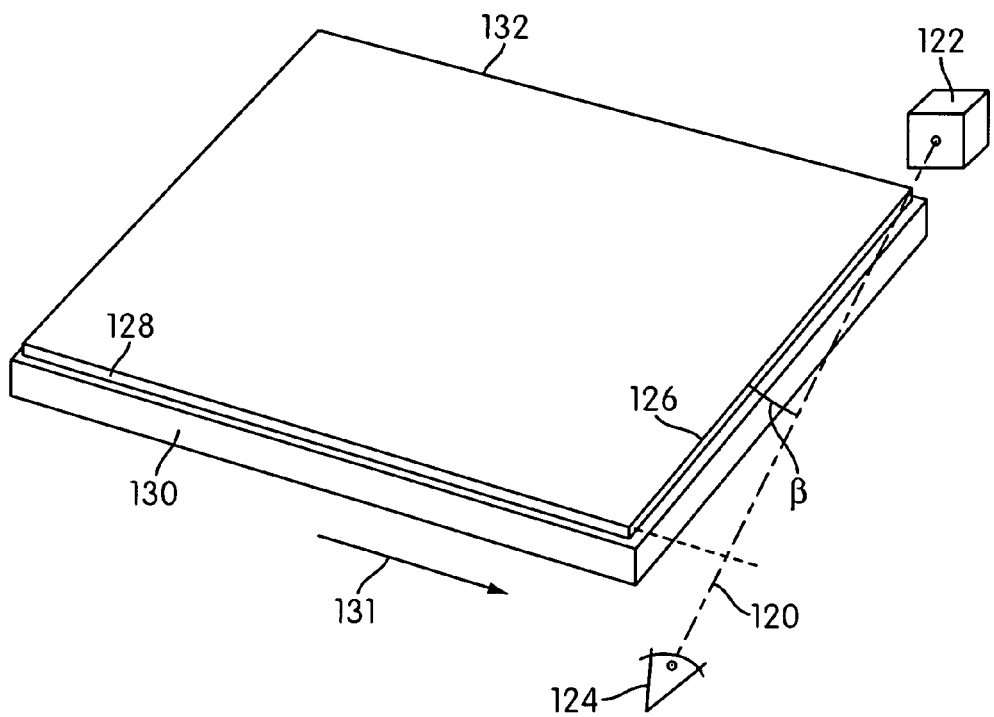
FIG. 8 depicts a perspective view of a substrate table and a substrate, including a particle detector system according to an embodiment of the invention.

Referring to FIG. 8, in an embodiment, rays of light 120 coming from a light source 122 and going to detector 124 are arranged at an angle $\beta$ to the front side 126 of a substrate 128, when seen in plan view. The substrate 128 is arranged on substrate table 130 and travels, during particle detection, in the direction of arrow 131, whereas the light source 122 and the detector 124 are stationary. The direction of travel of the substrate 128 is essentially parallel to a side 132 of the substrate 128.

In practice, the angle $\beta$ (FIG. 8) may be in the order of +/−10 to 20 mrad, and is composed of an angular error in the front side (the deviation from a perpendicular orientation relative to the side 132) and a selected angle to create sufficient measuring points on the front side of the substrate. A frame rate of the detector is chosen such that, dependent on the travel rate of the substrate 128, at least 50 frames are obtained at the front side 126 of the substrate. This way, tolerances of the measurement system are leveled to provide an improved detection and definition of the front side of an approaching substrate.

The above-described first embodiment has the following benefits:

- the measurement system uses light rays, thus obviating the need to contact the substrate surface, which would incorporate the risk of scratching the substrate surface;
- the measurement system covers a relatively wide detection area. The whole width of the substrate surface may be illuminated and measured at once;
- the measurement is relatively fast, thus allowing the above mentioned high travel rates of the substrates;
- the measurement system provides a reliable particle detection, which is mainly independent of the optical properties of the particles and/or contamination, such as scattering of light at the particle surface etc.;
- the measurement allows a determination of the particle height, thus obviating the need for further calculations incurring corresponding delay;
- the measurement system is relatively inexpensive, due to the use of a single light source and a single detector array to cover the entire width of the substrate.
- due to the small angle α the detector accuracy may be relatively low to still allow reliable particle detection. Reference is made to the above description in relation to FIG. 7;
- the measurement is essentially independent from the absolute height of the substrate surface. In other words, the measurement is independent on the distance between the substrate surface and the measurement system, as the system only measures the extension of dark areas generated by particles on the substrate surface. The measurement thus does not rely on an absolute distance measurement. This extension is related to the particle height, as explained above.

To cover the complete width of a substrate, two or more of the above-described particle detectors may be combined. The particle detector system according to embodiments of the invention is particularly beneficial and relatively inexpensive when the substrates are relatively small, i.e., having a width in the order of 1 m or below.

Although specific reference may be made in this text to the use of lithographic apparatus in the manufacture of a specific device (e.g., an integrated circuit or a flat panel display), it should be understood that the lithographic apparatus described herein may have other applications. Applications include, but are not limited to, the manufacture of integrated circuits, integrated optical systems, guidance and detection patterns for magnetic domain memories, flat-panel displays, liquid-crystal displays (LCDs), thin-film magnetic heads, micro-electromechanical devices (MEMS), etc. Also, for instance in a flat panel display, the present apparatus may be used to assist in the creation of a variety of layers, e.g., a thin film transistor layer and/or a color filter layer.

The term "lens," where the context allows, may refer to any one or combination of various types of optical components, including refractive, reflective, magnetic, electromagnetic and electrostatic optical components.

The terms "a" or "an," as used herein, are defined as one or more than one. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly, and not necessarily mechanically.

Embodiments of the invention may at least partly take the form of a computer program containing one or more sequences of machine-readable instructions describing a method as disclosed above, or a data storage medium (e.g., semiconductor memory, magnetic or optical disk) having such a computer program stored therein. A program, computer program, or software application may include a subroutine, a function, a procedure, an object method, an object implementation, an executable application, an applet, a servlet, a source code, an object code, a shared library/dynamic load library and/or other sequence of instructions designed for execution on a computer system.

Embodiments of the present invention are disclosed herein. However, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention. Modifications may be made to the invention as described without departing from the spirit and scope of the claims set out below.

What is claimed is:

1. A lithographic apparatus arranged to transfer a pattern from a patterning device onto a substrate, the apparatus comprising:
    a projection system configured to project a patterned radiation beam onto a target portion of the substrate;
    a controllable actuator configured to adjust a distance between the projection system and the substrate;
    a particle detector system configured to detect a particle on a surface of the substrate, the particle detector system comprising
        illumination optics configured to direct radiation to a detection area of the surface of the substrate,
        detection optics configured to receive radiation from the detection area of the surface of the substrate, and
        a detector coupled to the detection optics and configured to produce at least one measurement signal;
    a processing system configured to determine a height of the particle from the at least one measurement signal, to generate a height excess signal if the height exceeds a threshold value, and to control the actuator in response to the height excess signal.

2. The lithographic apparatus of claim 1, further comprising a radiation source to generate the radiation, wherein the radiation source has a small numerical aperture.

3. The lithographic apparatus of claim 1, wherein the illumination optics are configured to direct the radiation to the detection area at an illumination angle between about 0–5 degrees.

4. The lithographic apparatus of claim 3, wherein the illumination optics are configured to direct the radiation to the detection area at an illumination angle between about 1–2 degrees.

5. The lithographic apparatus of claim 3, wherein the detection optics have a center line, and a plane of the detector is directed at a detector angle between about 0–5 degrees to the center line of the detection optics, and wherein the detector angle is essentially equal to the illumination angle.

6. The lithographic apparatus of claim 1, wherein the radiation directed by the illumination optics to the detection area comprises essentially parallel rays of light.

7. The lithographic apparatus of claim 1, wherein the illumination optics are arranged near one side of the substrate, and the detection optics are arranged near an opposite side of the substrate.

8. The lithographic apparatus of claim 7, the particle detector system further comprising a dummy substrate part aligned with, and adjacent to said opposite side of the substrate.

9. The lithographic apparatus of claim 7, the particle detector further comprising a dummy construction part aligned with, and adjacent to said opposite side of the substrate, wherein the dummy construction part is provided with a plurality of spaced non-reflecting lines essentially parallel to said opposite side of the substrate.

10. The lithographic apparatus of claim 1, wherein the detection optics are telecentric.

11. The lithographic apparatus of claim 1, wherein the detection optics have a small numerical aperture.

12. The lithographic apparatus of claim 1, wherein the detection optics comprise a first lens to focus the radiation from the detection area.

13. The lithographic apparatus of claim 12, wherein the detection optics comprise a second lens to project the radiation focused by the first lens onto the detector.

14. The lithographic apparatus of claim 13, wherein the second lens of the detection optics has a smaller diameter than the first lens of the detection optics.

15. The lithographic apparatus of claim 1, wherein the detection optics have a center line, and a plane of the detector is directed at an angle between about 0–5 degrees to the center line of the detection optics.

16. The lithographic apparatus of claim 15, wherein the detection optics have a center line, and a plane of the detector is directed at a detector angle between about 1–2 degrees to the center line of the detection optics.

17. The lithographic apparatus of claim 1, wherein the detector comprises an array of detector elements.

18. The lithographic apparatus of claim 17, wherein the array is a CCD array.

19. The lithographic apparatus of claim 1, wherein the particle detector comprises a Scheimpflug arrangement of the detection optics and the detector.

20. The lithographic apparatus of claim 1, further comprising a substrate support configured to support the substrate, the substrate support being movable in a direction of conveyance.

21. The lithographic apparatus of claim 20, wherein the illumination optics are configured to direct the radiation to the surface of the substrate at an angle between about 0–1 degree to the direction of conveyance.

22. A particle detector system to detect a particle on a surface of a substrate, the particle detector system comprising:
   illumination optics configured to direct radiation to a detection area of the surface of the substrate;
   detection optics configured to receive radiation from the detection area of the surface of the substrate;
   a detector coupled to the detection optics and configured to produce at least one measurement signal; and
   a processing system coupled to the detector, the processing system configured to determine a height of the particle from the at least one measurement signal, to generate a height excess signal if the height exceeds a threshold value, and to control an actuator that is adapted to adjust a distance between a projection system and a substrate, the projection system adapted to project a pattern onto the substrate.

23. A device manufacturing method comprising:
   projecting a patterned beam of radiation on a surface of a substrate with a projection system;
   detecting a particle on the surface of the substrate, the detecting including:
      directing radiation to a detection area of the surface of the substrate,
      detecting radiation from the detection area of the surface of the substrate,
      producing at least one measurement signal from the detected radiation,
      determining a height of the particle from the at least one measurement signal, and
      generating a height excess signal if the height exceeds a threshold value, and
   adjusting a distance between the projection system and the substrate if the height exceeds the threshold value.

24. The method of claim 23, wherein the radiation is directed to the detection area at an angle between about 0–5 degrees.

25. The method of claim 23, further comprising:
   arranging the substrate on a substrate support;
   moving the substrate in a direction of conveyance,
   wherein the radiation is directed to the detection area at an angle near 90 degrees to the direction of conveyance.

26. The method of claim 23, wherein detecting the radiation from the detection area of the surface of the substrate is performed under a Scheimpflug condition.

* * * * *